United States Patent [19]

Cosmai

[11] Patent Number: 4,850,967
[45] Date of Patent: Jul. 25, 1989

[54] PORTABLE ENDERMIC INJECTOR

[75] Inventor: Pietro Cosmai, Gorizia, Italy

[73] Assignee: SICIM SpA, Romans D'Isonozo, Italy

[21] Appl. No.: 62,807

[22] Filed: Jun. 15, 1987

[30] Foreign Application Priority Data

Jun. 17, 1986 [IT]  Italy ................. 83373 A/86
Aug. 1, 1986 [IT]  Italy ................. 83389 A/86
Oct. 8, 1986 [IT]  Italy ................. 83421 A/86

[51] Int. Cl.⁴ .................................................. A61M 11/00
[52] U.S. Cl. ....................................... 604/68; 604/134
[58] Field of Search ......................... 604/68, 134–136, 604/71, 72

[56] References Cited

U.S. PATENT DOCUMENTS

| | | |
|---|---|---|
| 2,653,602 | 9/1953 | Smoot .................................. 604/68 |
| 2,717,597 | 9/1953 | Hein, Jr. . |
| 2,737,946 | 9/1954 | Hein, Jr. . |
| 2,762,369 | 9/1956 | Venditty .............................. 604/68 |
| 2,800,903 | 7/1957 | Smoot .................................. 604/68 |
| 2,928,390 | 7/1957 | Venditty et al. . |
| 3,330,276 | 10/1963 | Gordon . |
| 3,330,277 | 8/1964 | Gabriels . |
| 3,507,276 | 4/1970 | Burgess .............................. 604/68 |
| 3,526,225 | 12/1970 | Isobe . |
| 3,557,784 | 1/1971 | Shields ............................... 604/68 |
| 3,714,943 | 2/1973 | Yanof . |
| 3,827,601 | 3/1973 | Magrath et al. . |
| 3,908,651 | 5/1974 | Fudge . |
| 4,165,800 | 8/1979 | Doherty et al. .................... 604/68 |
| 4,266,541 | 5/1981 | Landau ............................... 604/68 |
| 4,530,695 | 7/1985 | Phillips et al. ..................... 604/134 |
| 4,623,332 | 11/1986 | Lindmayer et al. ............... 604/68 |
| 4,626,242 | 12/1986 | Fejes et al. ........................ 604/68 |
| 4,642,095 | 2/1987 | Dettbarn et al. ................... 604/68 |
| 4,722,728 | 2/1988 | Dixon ................................. 604/68 |

FOREIGN PATENT DOCUMENTS 0114792 8/1984 European Pat. Off. .
1333215 10/1973 United Kingdom ................ 604/68

Primary Examiner—Stephen C. Pellegrino
Assistant Examiner—Ralph Lewis
Attorney, Agent, or Firm—Flynn, Thiel, Boutell & Tanis

[57] ABSTRACT

Portable endermic injector of a mechanical type which comprises an aspiration and containment chamber, an assembly (12) to aspirate and to store, a cocking and trigger assembly (13) and an assembly (14) to read the quantity aspirated. A containment assembly (11) comprises the aspiration and containment chamber and a piston (19) and is screwed onto a frontal container (15). The assembly (12) to aspirate and to store energy comprises apparatus to regulate the pre-loading of a spring assembly (28) which includes spacer rings (226) and apparatus (15-23) having variable axial reciprocal positions. The reader assembly (14) comprises a threaded portion (46) and a slider (47) cooperating with a graduated area (50).

20 Claims, 3 Drawing Sheets

PORTABLE ENDERMIC INJECTOR

This invention concerns an endermic injector of a type loaded by hand and with a storage of ejection force by means of spring elements. The injector according to the invention serves to inject pharmaceutical substances, such as insulin, without using a needle.

Many types of endermic injectors of the above kind are known.

U.S. Pat. No. 2,717,597 discloses an injector apparatus having a very complicated structure. This injector comprises in the area of its head a chamber to hold a special (vial) containing the medicament.

This apparatus entails noteworthy difficulties when being loaded since it cannot be loaded from outside but has to be partly dismantled for the introduction of the special phial.

Moveover, the apparatus comprises an inadequate safety system and is not fully hygienic as it is difficult to clean; besides, the medicament cannot be drawn from normal, commercially available phials.

Furthermore, the dose to be injected is unchangeable or else, if the dose is to be varied, it is necessary to employ phials of different capacities.

U.S. Pat. No. 2,737,946 also discloses an injector having a very complicated structure. Here also the medicament is held in a special phial, which is inserted near the head of the injector when it is to be used. The phial is complex and hard to embody and entails problems of safety, cleanliness and a proper seal.

This patent, like the previous one, does not permit the medicament to be loaded from the outside with normal, commercially available phials nor every required dose to be injected.

Moreover, the pressure which forces the medicament through the small outlet hole is provided by a gas which has been compressed beforehand during loading and which is kept momentarily in a chamber within the injector itself.

The high pressures to which the gas has to be compressed involve difficulties of a good seal and impair the working life of the apparatus.

U.S. Pat. No. 2,928,390 discloses an injector which enables the medicament to be loaded, measured, and drawn from normal, commercially available phials. The injector works in two stages; the first and faster stage enables the medicament to overcome the compactness of the skin, while the second and slower stage permits an excellent penetration of the medicament.

The injector has an exceptionally complex structure, which makes it heavy, hard to handle and too expensive; moreover, its sterilization and maintenance cause great problems. Compressed air is employed to load the springs providing the thrust for the cylinders which generate the outgoing pressure of the medicament; this entails a considerable drawback since the injections can only be performed when an independent unit to provide compressed air is available. Furthermore, a person suffering from diabetes certainly cannot carry such a device with him.

U.S. Pat. No. 3,330,276 discloses a device which can measure and load the medicament from without and can draw it from normal, commercially available phials, but which has a very heavy and complex structure, is difficult to handle and has a very complicated system for installing and positioning the phial, thus involving great difficulties in using and carrying the device.

The phial is not properly protected and is prone to breakage, thus restricting the ability to carry the device. Moreover, only one type of medicament can be loaded into this device at a time; this fact restricts its use since some patients, such as diabetics, require injections consisting of components drawn from different phials and advantageously mixed before being injected.

In this patent the thrust exerted by springs to eject the medicament is not capable of being strong enough, above all owing to the complexity and weight of the parts of which the device consists. Besides, it is not possible to regulate the power of the assembly which propels the medicament.

A great shortcoming of this device is the inclusion of an air filter fitted near the phial holder. This filter is needed to maintain the desired pressure within the phial itself during loading of the medicament and also to maintain sterile conditions within the phial.

Moreover, this patent entails difficulties in dismantling for sterilization and maintenance in that servicing keys are required.

A further drawback is the fact that the phial can explode during ejection if the valve is left in the drawing position accidentally, Moreover, the device has to be fully unloaded after ejection before it can be re-loaded.

U.S. Pat. No. 3,330,277 discloses a variant of U.S. Pat. No. 3,330,276, but this variant does not apply any substantial functional changes or improvements as regards the shortcomings of U.S. Pat No. 3,330,276.

U.S. Pat. No. 3,526,225 discloses an injector to be used in conjunction with an outside source of compressed air. This invention is therefore suitable only for use in a surgery for multiple vaccinations and does not provide for mixture of medicaments.

U.S. Pat. No. 3,714,943 concerns a device which can lodge within itself a plurality of special phials the contents of which can be injected one by one. In this case it is not possible to load the medicament from outside and to use normal, commercially available phials.

Moreover, the pressure needed to eject the medicament is generated by a gas compressed beforehand in a chamber inside the device itself. As we said earlier, this entails problems of a proper seal.

U.S. Pat. No. 3,827,601 discloses a device operated by hand and of no great power, this device not being relevant for the purposes of our invention.

U.S. Pat. No. 3,908,651 discloses an injector which enables the measurement and loading of the medicament to be performed outside, the medicament being drawn from normal, commercially available phials. This injector comprises an injection head of a complex structure together with a safety device which prevents the medicament flowing back into the phial in the event of wrong operation.

The injector includes also a very complicated fixture system and is suitable to administer the medicament from only one phial at a time; this is a great drawback, as we said earlier. Moreover, the patent does not disclose how the injecting action is achieved, graduated and developed. Another drawback lies in the fact that the injector has to be dismantled with servicing keys.

EP No. 0114792 discloses an endermic injector suitable to draw from two external phials the material to be injected. It comprises a particularly complex system to modify and clean the injecting assembly. Moreover, it has a considerable bulk and is therefore not suitable for personal use and for being carried by its user.

The present invention tends to overcome the shortcomings of the prior art by providing many benefits and advantages.

It is thus a purpose of the invention to provide an injector which enables the components being injected to be loaded quickly in desired quantities during the loading phase.

It is also a purpose of the invention to provide a very compact injector which can be easily carried and be combined with an outside assembly that contains and distributes the medicament to be loaded.

A further purpose of the invention is to provide an endermic injector which is light and easy to use and needs little maintenance.

Another purpose of the invention is to provide an injector with a containment assembly which is simple and easy to replace, dismantle and sterilize.

Yet another purpose is to provide a device which can be set and regulated easily, even by unskilled persons, so as to adapt the injecting action to the various requirements of the user's skin.

It is also a purpose of the invention to embody a safe device which cannot be actuated accidentally.

A further purpose is to provide a device in which it is easy to check the quantity loaded.

The invention also has the purpose of facilitating the ejection actuation without transmitting vibrations or jerks to the apparatus.

The present invention tends to overcome the drawbacks of the known art by offering an endermic injector which is light, easy to handle, regulate and sterilize, easy to actuate and which provides easy reading of the value of medicament loaded.

According to the invention the container for the liquid to be injected forms part of a containment assembly which cooperates with a phial container of a removable type that does not form part of this invention.

The containment assembly comprises means which are secured momentarily to the phial container and enable the required doses to be loaded.

Moreover, the containment assembly is so formed that it can be fully replaced in order to enable it to be prepared quickly and to be dismantled completely and sterilized without any need for haste.

The assembly to aspirate and to store energy is provided with a double regulation capability so as to cover a very wide range of requirements of the human skin, for every person's skin possesses different characteristics and requirements and the pressure of an injection must therefore be adapted to the individual in question.

According to the invention two adjustments can be made, a first rough adjustment and a second fine adjustment suited to the specific skin requirements.

Moreover, the aspiration assembly comprises means to show the quantity loaded (by aspiration), the means being easy to read and thus preventing mistakes or confusion.

In a variant means are provided to prevent accidental actuation of the injection, thus obviating undesired ejections with loss of medical sustances.

According to the invention actuation means are included which are suitable to avoid creation of vibrations in the injector.

In a variant these actuation means can be operated axially so that any vibration or movements caused by actuation are transmitted axially.

The invention is therefore embodied with a portable endermic injector of a mechanical type which comprises an aspiration and containment chamber, an assembly to aspirate and to store, a cocking and trigger assembly and an assembly to read the quantity aspirated and is characterized in that:

a containment assembly comprising the aspiration and containment chamber and a piston is screwed onto a frontal container, the assembly to aspirate and to store energy comprises means to regulate the pre-loading of a spring assembly which consist of spacer rings and means having variable axial reciprocal positions, and the reader assembly comprises a threaded tract and a slider cooperating with a graduated area.

The attached figures, which give two non-restrictive preferred embodiments, show a lengthwise section of an injector according to the invention and a variant thereof.

Figure 1:
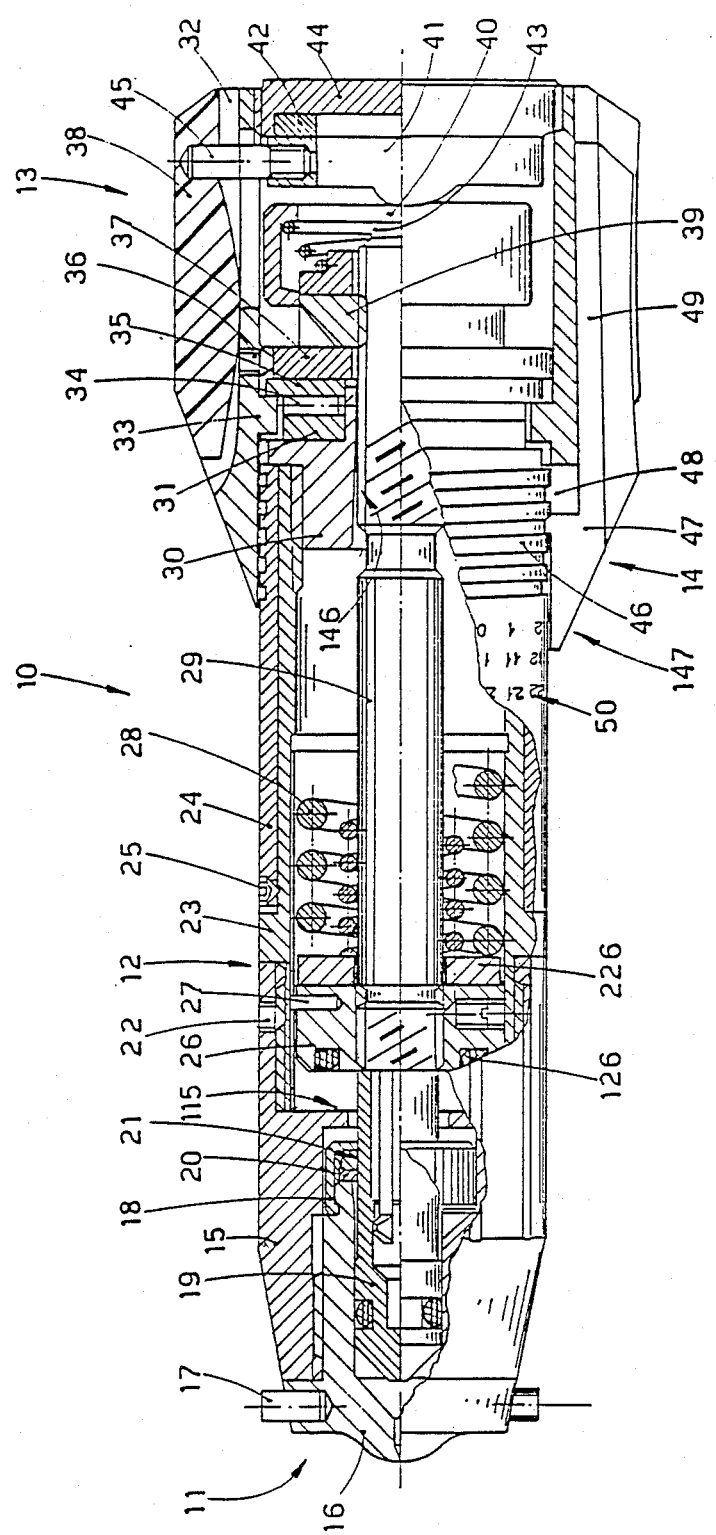
FIG. 1 is a side view, partially broken away in central cross section, showing an injector device embodying the invention.

FIG. 1 shows an injector device which comprises a containment assembly 11, an assembly 12 to aspirate and to store energy, a trigger assembly 13 and a reader assembly 14. The containment assembly 11 is screwed onto a frontal container 15 owing to an injection head 16.

The injection head 16 comprises rods 17 which assist the screwing and unscrewing of the containment assembly 11 and make possible the anchorage of an external assembly which mixes and delivers liquid to be aspirated.

The containment assembly 11 consists not only of the injection head 16 but also of a piston 19, which slides in an aspiration and containment chamber, and of a rear containment cap 18, abutment ring 20 and packing 21.

Every part of the containment assembly 11 can be dismantled, and the assembly can be easily and quickly sterilised. Moreover, the containment assembly 11 can be easily replaced with an identical assembly or with another having a greater or smaller loading capacity and therefore a different capability.

The connection of the piston 19 to a shaft 29 is of a known type and provides a quick and easy axial connection.

The aspiration and storage assembly 12 comprises the shaft 29 bearing an abutment ring 26.

The shaft 29 and ring 26 can only move axially owing to the inclusion of a guide pin 27 which runs in an appropriate lengthwise groove inside a containment and guide sleeve 23.

Springs 28 thrust against the abutment ring 26 and also press against a perforated cap 30. If it is desired to enhance the action of the springs 28, their pre-loading is altered by placing spacer rings 226 of various thicknesses between the springs 28 and the abutment ring 26. These spacer rings 226 provide a rough adjustment and can also be placed between the springs 28 and the perforated cap 30.

At the forward end of the run of the shaft 29 the abutment ring 26 abuts against an inner face 115 of the frontal container 15.

The inclusion of a resilient ring 126 serves for damping and silencing purposes.

The frontal container 15 can be screwed onto, or unscrewed from, the containment and guide sleeve 23; the figure shows them screwed together. The reciprocal desired positions of the containment sleeve 23 and container 15 are secured by a dowel 22 which cooperates with one or more lengthwise grooves in the containment and guide sleeve 23.

Fine adjustment of the pre-loading of the springs 28 and therefore of the power of injection is obtained by altering the reciprocal positions of the sleeve 23 and container 15.

Figure 2:
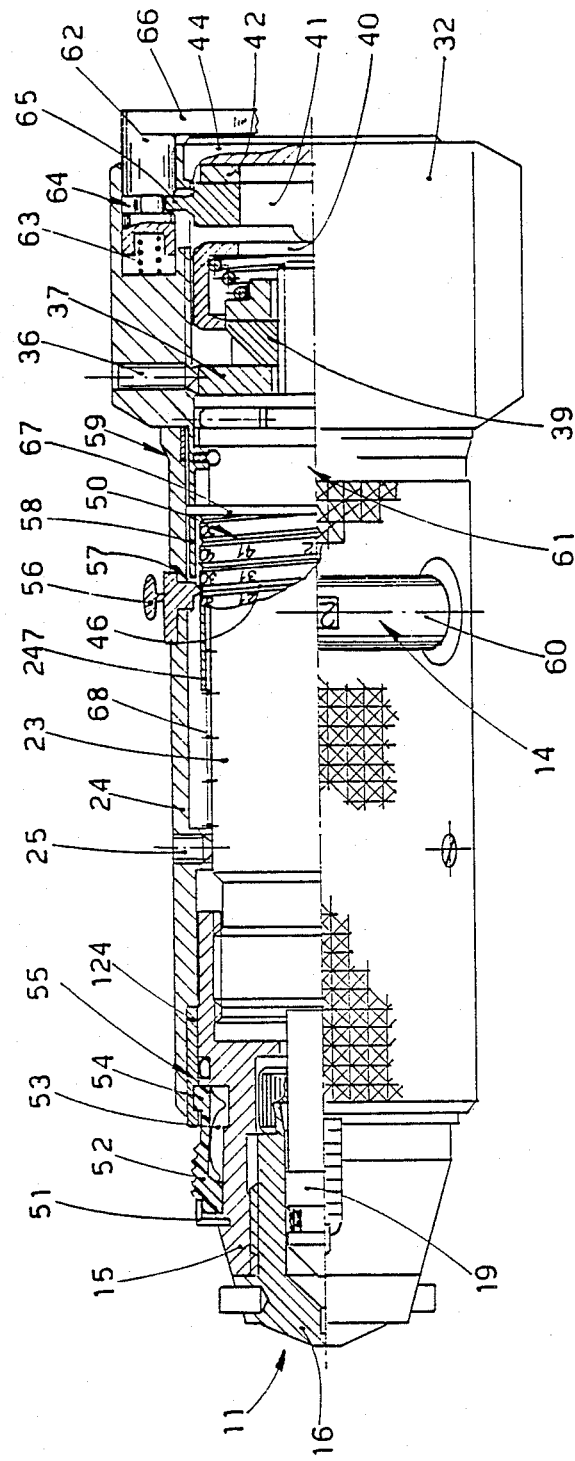
FIG. 2 is a view generally similar to FIG. 1 but showing a modification.
Figure 5:
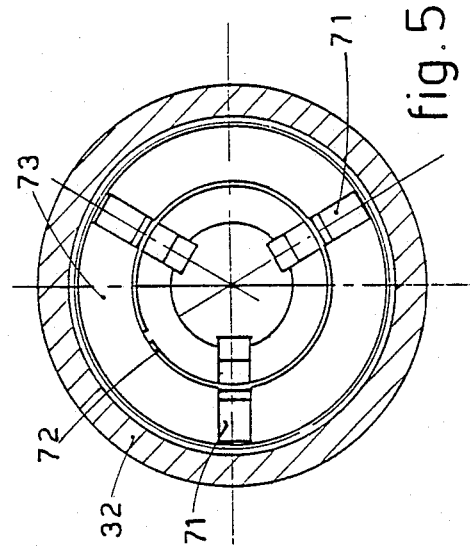
FIG. 5 is a cross-sectional view substantially taken on the chain line V—V of FIG. 3.

In a variant the frontal container 15 is screwed onto the containment and guide sleeve 23 and is partially surrounded by a reader sleeve 24 (FIG.2).

The desired fine adjustment is obtained by screwing the container 15 on the containment sleeve 23 to a greater or lesser extent.

Grooves 55 located along a circumference in an auxiliary sleeve 124 solidly fixed to the reader sleeve 24 are provided for the positioning of the frontal container 15 in relation to the containment sleeve 23. A protrusion 54 of a push button 52 resiliently thrust towards the groove 55 in question by a spring 53 cooperates in these grooves 55.

The push button 52 is secured with an engagement tooth 51; if the push button 52 is operated, the protrusion 54 is freed from the groove 55 in question and the frontal container 15 can be rotated in relation to the containment sleeve 23.

The containment sleeve 23 and reader sleeve 24 are solidly fixed together with a dowel 25.

Suitable marks on the container 15 cooperate with the front edge of the auxiliary sleeve 124 and show the value of the adjustment.

Thus, there are two systems to regulate the power of injection, of which one system provides rough regulation with the spacer rings 226 placed, or not placed, between the abutment ring 26 and the springs 28, whereas the other system provides fine adjustment by screwing or unscrewing the frontal container 15 on the containment sleeve 23.

The loading and ejection system or cocking and trigger assembly 13 is known and is described in EP No. 0114792. This system, which cooperates with a threaded portion 146 on the shaft 29, comprises an annular container 37 fixed solidly to a hand grip 32 by a dowel 36.

The annular container 37 includes radial hollows within which there can slide teeth 39 kept in the cocked position by an actuator 40. The actuator 40 is pressed against an annular lever 41 by spring means 43; the annular lever is normally rested on a rear abutment ring 42 which cooperates with a stopper 44.

The annular lever 41 is connected to a push button 38 by a pin 45. If the push button 38 is operated, the lever 41 is displaced and pushes the actuator 40 forwards.

Being pushed forward, the actuator 40 frees the teeth 39, which become partially located within the actuator 40 and free the shaft 29, which is thrust forward by the spring s 28.

The inclined surface on the teeth 39 has the result that, with the actuator 40 moved back once more, the teeth 39 are re-positioned in the cocking position of anchorage to the threaded portion 146 on the shaft 29.

In a variant (FIG. 2) the annular lever 41 comprises a prong 65 that cooperates with an annular groove 64 comprised on a trigger 62 kept resiliently in position by springs 63. The trigger 62 can rotate on its axis and includes a safety arm 66. When the safety arm 66 is rotated towards the stopper 44, the trigger 62 cannot move axially even if it is operated, whereas when the arm 66 is rotated outwards, the trigger 62 can be actuated and the injector can be made to function.

This system provides safety against wrong operation and enables the injector to be carried already prepared to perform injections without any risk of accidental functioning.

In a further variant shown in FIGS. 3 to 6 a tripping system is provided which acts directly along the axis of the injector and does not create unacceptable sideways displacements or movements.

In this variant a trigger 162 is positioned axially to the injector 10 on the rear thereof. This trigger 162 comprises on its outer surface some means to enable the trigger to be rotated by an angle with the ball of a finger or thumb or with a coin, for instance.

The field of angular rotation of the trigger 162 is determined by cooperation of a pin 74 with a peripheral hollow 69 comprised in the trigger 162 itself.

Figure 6:
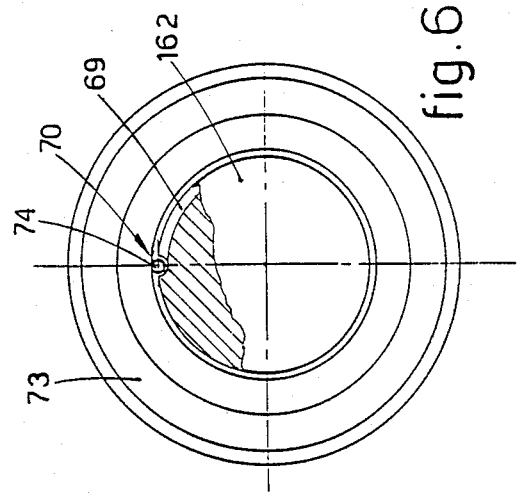
FIG. 6 is a partially broken right end view of the modified apparatus of FIGS. 3 and 4.
Figure 3:
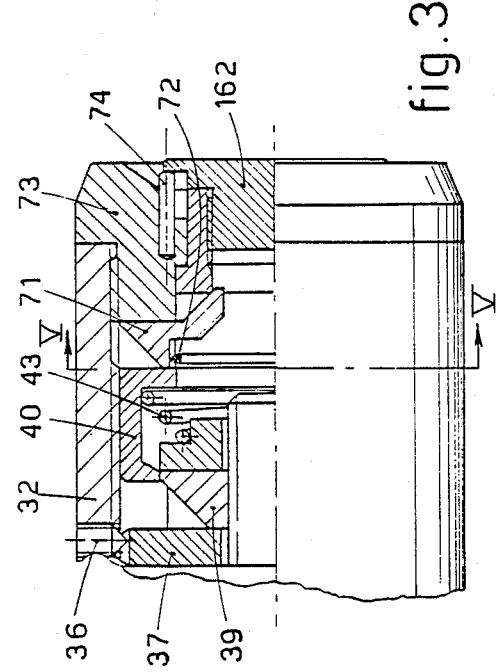
FIG. 3 is a fragmentary side view partially broken in central cross section and showing the tripping system of a further modified embodiment.
Figure 4:
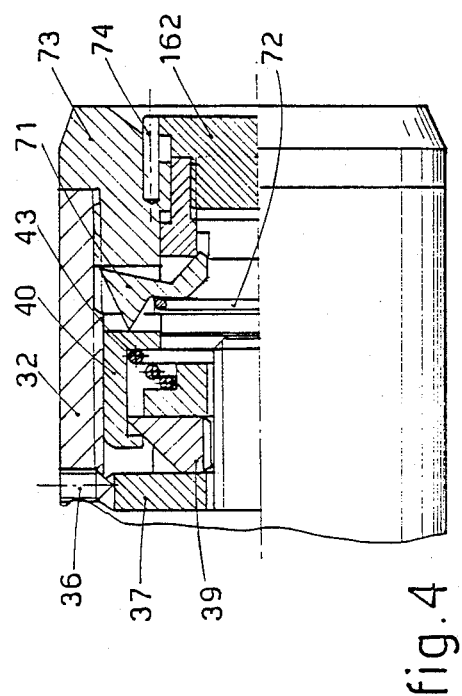
FIG. 4 is a view similar to FIG. 3 with parts thereof in a different operating position (trigger moved inwardly).

An indentation 70 is included at one end of the peripheral hollow 69 and enables the trigger 162 to move axially without being opposed by the pin 74 (FIG. 6 and FIGS. 3 and 4).

When moved axially, the trigger 1 62 acts on levers 71 positioned by a ring 72. In their inactive phase the levers 71 are supported on one side by a sleeve 73, which comprises hollow radial seatings in which the levers 71 are lodged (FIGS. 3 and 5), and are rested on their other side against the rear on the actuator 40 (FIG. 3).

When the trigger 162 is moved axially inwards, it acts against the levers 71 (FIG. 4), thus augmenting their arms and therefore displacing the actuator 40. When the actuator 40 is moved forwards, the teeth 39 are freed and ejection takes place.

In the example shown two rings 31 and 35 with a frontal bearing 34 positioned between them are included between the rearward perforated cap 30 and annular container 37. This enables the hand grip 32 to rotate and meet with only friction of the rotary motion.

The hand grip 32 transmits rotary motion to the annular container 37 and is prevented from moving axially by an annular tooth 33.

In the example shown the replaceable reader sleeve 24, which can be anchored to the containment and guide sleeve 23 by the dowel 25, is positioned coaxially with this containment sleeve 23 and includes graduation marks 50 to be adapted to the containment assembly 11 installed.

A threaded portion 46 is included in the rear terminal part of the reader sleeve 24; the pitch of the threads 46 is cooerdinated with the pitch of the threads 146 on the shaft 29. In this way the shaft 29 is retracted by one pitch of its threaded portion 146 with each revolution of the hand grip 32.

A slider 47, which runs on guides 49 in the hand grip 32, is anchored by a tooth 48 to the threaded portion 46 of the reader sleeve 24.

A pointer 147 on the slider 47 is therefore displaced lengthwise on the reader sleeve 24 while it rotates together with the hand grip 32.

Since there is correlation between the pitch of the threads 46 of the reader sleeve 24 and the pitch of the threads 146 on the shaft 29, with each revolution of the hand grip 32 the pointer 147 too is displaced by a value correlated with the pitch of the threads 146 on the shaft 29.

This system enables a reader assembly 14 to be provided which is very simple and easy to use.

In a variant an annular interspace, within which an annular slider 247 thrust by a spring 68 against the hand grip 32 is lodged, is provided between the reader sleeve 24 comprising a reader hole 14 and the containment sleeve 23.

The annular slider 247 has on its surface a threaded portion 46, the values of the graduation markings 50 being visible in the interspaces between the threads of the threaded portion 46.

The annular slider 247 comprises terminally an abutment ring 67 which, being able to slide axially, cooperates with a guide rod 58 solidly fixed to the hand grip 32.

When the hand grip 32 is rotated, it sets in rotation the guide rod 58, which in turn sets in rotation the annular slider 247, which is able to slide axially and remains always in torsional engagement with the guide rod 58.

A resilient blade 60 is comprised on the reader sleeve 24 and bears a reader catch 56 having an engagement tooth 57, which is able to cooperate with the threaded portion 46. Since the tooth 57 is unable to move axially, if the hand grip 32 is rotated, it sets in rotation by means of the guide rod 58 the annular slider 247, which is able to move axially owing to cooperation between the tooth 57 and threaded portion 46.

Through a window in the reader assembly 14 it is possible to see the graduation values 50 slide.

After injection has taken place, the reader catch 56 is raised and releases the tooth 57 from the threaded portion 46 and the spring 68 brings the annular slider 247 back to zero.

The inclusion of a spherical positioner 59 cooperating with positioner hollows 61 enables the rotation and the progress of the filling to be felt.

By means of this variant it is possible not only to set the indicator easily to zero but also to obviate jutting parts which become readily worn, entangled, broken, etc.

I claim:

1. Portable endermic injector of a mechanical type, comprising:
    a frontal container (15);
    a containment assembly (11) fitted in said frontal container;
    a containment and guide sleeve (23) which extends rearward from the frontal container (15);
    an aspiration and storage means (12) including an abutment ring (26) axially reciprocable in said containment and guide sleeve (23), means (27) preventing rotation of said ring in said containment and guide sleeve (23), an actuation shaft (29) fixed to said ring (26) for axial reciprocation therewith in said containment and guide sleeve (23), and a spring assembly (28) cooperable with said actuation shaft (29) for urging same axially toward said containment assembly (11);
    cocking and trigger means (13) actuable to momentarily anchor to said actuation shaft (29);
    means (14) associated with at least one of said frontal container (15) and containment and guide sleeve (23) for reading the quantity aspirated;
    in which:
    said containment assembly (11) includes an injection head (16) facing forward from said frontal container (15), an aspiration and containment chamber in said injection head (16) for holding liquid to be injected, and a piston (19) slidable in said aspiration and containment chamber and connected to said actuation shaft (29);
    said aspiration and energy storage means (12) comprises means for regulating the preloading of said spring assembly (28) and comprising a
    (A) spacer ring (226) insertable between said spring assembly (28) and said abutment ring (26), and
    (B) means axially adjustably interconnecting said frontal container (15) and said containment and guide sleeve (23);
    said reading means (14) comprises a threaded track (46) on a reader sleeve (24) disposed outside of said containment and guide sleeve (23), graduation marks (50) and means locating same on a surface disposed radially outboard of one of said frontal container (15) and containment and guide sleeve (23), and slider means (47, 247) threadedly adjustable on said threaded track (46) and cooperable with said graduation marks (50) for indicating the quantity of a medicament injected by said injector.

2. Injector as claimed in claim 1, in which the injection head (16) is screwed onto the frontal container (15) and on which is screwed a rear containment cap (18) that intercepts the piston (19) axially.

3. Injector as claimed in claim 2, in which a packing is fixed with respect to the rear containment cap (18) and injection head (16) and slidably receives the piston (19).

4. Injector as claimed in claim 2, in which the injection head (16) comprises, at its front, a nose protruding forward from said frontal container (15) and anchorage rods (17) extending radially out from said nose.

5. Injector as claimed in claim 1, in which a plurality of spacer rings (226) are placed between the spring assembly (28) and the abutment ring (26).

6. Injector as claimed in claim 1, including a perforated cap (30) surrounding said actuation shaft (29) and surrounded by said sleeve (23) at the end thereof remote from said abutment ring (26).

7. Injector as claimed in claim 1, in which the means axially adjustably interconnecting the frontal container (15) and the containment and guide sleeve (23) is a threaded connection, and including a reciprocal fixture dowel (22) insertable in said threaded connection to lock said container (15) and sleeve (23) is a desired relative axial position.

8. Injector as claimed in claim 1, in which the means axially adjustably interconnecting the frontal container (15) and the containment and guide sleeve (23) includes a resiliently thrust, reciprocal fixture push button (52).

9. Injector as claimed in claim 1, in which the means axially adjustably interconnecting the frontal container (15) and the containment and guide sleeve (23) comprises a threaded connection which is axially adjustable.

10. Injector as claimed in claim 1, in which the slider (47) slides on lengthwise guides (49) included in a hand grip (32) located on the end of said sleeve (23) remote from said frontal container (15).

11. Injector as claimed in claim 1, in which the slider means (47) comprises a tooth (48) that cooperates with the threaded track (46).

12. Injector as claimed in claim 11, in which the slider means comprises an annular slider (247) which is resiliently and axially thrust by a spring (68) towards a hand grip (32) and is positioned between the reader sleeve (24) and the containment sleeve (23).

13. Injector as claimed in claim 12, in which the reader sleeve (24) with the reader assembly (14) comprises a reader catch (56) with an engagement tooth (57) able to cooperate with the threaded track (46).

14. Injector as claimed in claim 13, in which the reader catch (56) is pressed resiliently against the annular slider (247).

15. Injector as claimed in claim 13, in which the pitch of the threaded track (46) is coordinated with the pitch of a second threaded track (146) on the actuation shaft (29).

16. Injector as claimed in claim 1, in which the graduation marks (50) cooperable with the slider (47-247) are proportioned directly to the volume of the aspiration and containment chamber in the containment assembly (11).

17. Injector as claimed in claim 1, in which the cocking and trigger means (13) includes an annular lever (41) which engages a two-positional trigger (62), both of which are disposed adjacent the end of the sleeve (23) remote from the frontal container (15), and means operatively connecting said annular lever (41) with the end of said actuation shaft (29) remote from said frontal container (15) for freeing the actuation shaft (29) to be shifted forward toward said containment assembly (11) by said spring assembly (28).

18. Injector as claimed in claim 1, including the trigger (62) comprises an annular groove (64) that cooperates with the annular lever (41) and with a safety arm (66), the trigger (62) being rotatable about its own axis.

19. Injector as claimed in claim 1 in which the cocking and trigger means (13) includes an actuator (40) adjacent the rear end of the actuator shaft (29) and means responsive to forward shifting of said actuator (40) for freeing the actuator shaft (29) to be shifted forward toward said containment assembly (11) by said spring assembly (28), an axially shiftable trigger (162) adjacent the rear end of said shaft and said actuator, and radial levers (71) interposed between said trigger (162) and actuator (40) for causing said forward shifting of said actuator (40) in response to axial shifting of said trigger (162), said trigger (162) also being rotatable on the axis of said shaft (29).

20. Injector as claimed in claim 19, in which the trigger (162) has an active position and a safe position, the active position being determined by the cooperation of an indentation (70) in the trigger (162) and a pin (174), and means supporting the pin (74) with respect to and to the rear of said reader sleeve (24).

* * * * *

UNITED STATES PATENT AND TRADEMARK OFFICE
CERTIFICATE OF CORRECTION

PATENT NO. : 4 850 967
DATED : July 25, 1990
INVENTOR(S) : Pietro Cosmai

It is certified that error appears in the above-identified patent and that said Letters Patent is hereby corrected as shown below:

Col. 8, line 57; change "sleeve (23) is a desired" to ---sleeve (23) in a desired---.

Col. 8, line 67-68; change "the slider (47) slides on" to ---the slider means (47) slides on---.

Col. 10, lines 7-8; change "claim 1, including the trigger (62)" to ---claim 17, in which the trigger (62)---.

Col. 10, line 27; change "and a pin (174)," to ---and a pin (74),---.

Signed and Sealed this

Thirteenth Day of November, 1990

*Attest:*

HARRY F. MANBECK, JR.

*Attesting Officer*    *Commissioner of Patents and Trademarks*